| United States Patent [19] | [11] Patent Number: 4,788,348 |
|---|---|
| Whittle | [45] Date of Patent: Nov. 29, 1988 |

[54] INSECTICIDAL ALKENES

[75] Inventor: Alan J. Whittle, Aldershot, England

[73] Assignee: Imperial Chemical Industries PLC, London, England

[21] Appl. No.: 84,199

[22] Filed: Aug. 12, 1987

[51] Int. Cl.$^4$ .................... C07C 43/257; C07C 43/20
[52] U.S. Cl. .................... 568/638; 568/637; 568/636
[58] Field of Search .................... 568/637, 638, 9, 636

[56] References Cited

U.S. PATENT DOCUMENTS

| 3,755,459 | 8/1973 | Diamond | 568/9 |
|---|---|---|---|
| 4,073,812 | 2/1978 | Bull et al. | 568/637 |
| 4,264,593 | 4/1981 | Sukman | 568/9 |
| 4,319,048 | 3/1982 | Bollag et al. | 568/9 |
| 4,532,355 | 7/1985 | Bollag et al. | 568/9 |
| 4,542,243 | 9/1985 | Umemoto et al. | 568/637 |
| 4,570,005 | 2/1986 | Nakatami et al. | 568/637 |
| 4,656,310 | 4/1987 | Bollag et al. | 568/9 |
| 4,705,900 | 11/1987 | Whittle | 568/637 |

FOREIGN PATENT DOCUMENTS

| 0125204 | 11/1984 | European Pat. Off. . |
|---|---|---|
| 0124369 | 11/1984 | European Pat. Off. . |
| 2502786 | 7/1976 | Fed. Rep. of Germany . |
| 3317908 | 12/1983 | Fed. Rep. of Germany . |
| 225135 | 12/1984 | Japan . |
| 1097543 | 11/1965 | United Kingdom . |
| 2085006A | 4/1982 | United Kingdom . |
| 2131424A | 6/1984 | United Kingdom . |

*Primary Examiner*—Werren B. Lone
*Attorney, Agent, or Firm*—Cushman, Darby & Cushman

[57] ABSTRACT

Compounds of formula $R^3$—CH=CH—$CR^1R^2$—CH$_2$OCH$_2R^4$ wherein $R^1$ and $R^2$ are H, alkyl or together form a cycloalkyl group with the adjacent carbon, $R^3$ is a substituted phenyl group, $R^4$ is an optionally substituted phenoxy phenyl group, and compositions containing them useful as insecticides, and compounds of formula HOCH$_2$—$CR^1R^2$—CH$_2$OCH$_2R^4$ and OCH—$CR^1R^2$CH$_2$OCH$_2R^4$, useful as intermediates therefor.

2 Claims, No Drawings

INSECTICIDAL ALKENES

This invention relates to novel ethers useful as insecticides and their preparation, to insecticidal compositions thereof and to methods of combating and controlling insect pests therewith.

In a first aspect the invention provides compounds of formula:

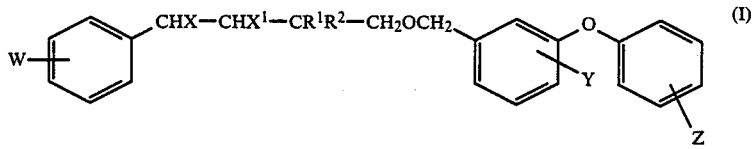

wherein W represents hydrogen or one or two substituents selected from halo, alkyl of up to four carbon atoms, alkoxy of up to four carbon atoms, and fluoroalkyl of up to four carbon atoms; X and $X^1$ both represent hydrogen or together represent a second bond between the adjacent carbon atoms; Y represents hydrogen or halogen; Z represents hydrogen, halogen or alkyl of up to four carbon atoms; and $R^1$ and $R^2$ each represent hydrogen or alkyl of up to four carbon atoms, or $R^1$ and $R^2$ together represent an alkylene group of from two to five carbon atoms.

Preferred compounds of formula I are those wherein W is selected from hydrogen, fluoro, chloro, methyl, methoxy, ethoxy or trifluoromethyl; X and $X^1$ each represent hydrogen or together represent a second bond between the adjacent carbon atoms; Y is hydrogen or fluoro; Z is hydrogen, and $R^1$ and $R^2$ are methyl or ethyl or together represent the group $-CH_2-CH_2-$.

More preferred compounds of formula I are those wherein W represents hydrogen or a 4-fluoro, 4-chloro, 4-methyl or 4-methoxy group, X and $X^1$ represent a second bond between the adjacent carbon atoms, Y is hydrogen or 4-fluoro, Z is hydrogen and $R^1$ and $R^2$ are both methyl. Such compounds contain a double bond giving rise to Z and E isomers. E isomers appear to be more insecticidally useful than Z isomers although products containing a mixture of Z and E isomers may also be useful, and the present invention includes within its scope all isomeric forms in isolation, and mixtures of isomers, of the compounds of formula I.

Particular examples of compounds of formula I are set out in Table I and II below. In Table I the compounds conform to the formula:

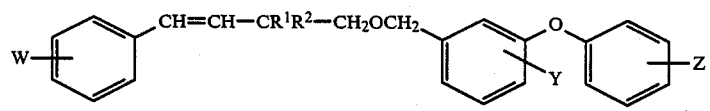

and in Table II to the formula:

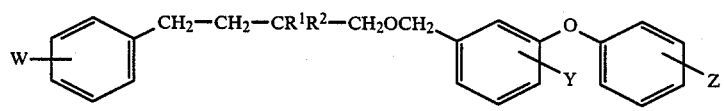

TABLE I

| Compound Number | W | $R^1$ | $R^2$ | Y | Z | Isomer or Isomer Ratio (E:Z) |
|---|---|---|---|---|---|---|
| 1 | 4-Cl | $CH_3$ | $CH_3$ | H | H | 1:1 |
| 2 | 4-Cl | $CH_3$ | $CH_3$ | H | H | Z |
| 3 | 4-$C_2H_5O$ | $CH_3$ | $CH_3$ | H | H | Z |
| 4 | 4-$C_2H_5O$ | $CH_3$ | $CH_3$ | H | H | E |
| 5 | 4-F | $CH_3$ | $CH_3$ | F | H | Z |
| 6 | 4-F | $CH_3$ | $CH_3$ | F | H | E |
| 7 | 4-Cl | $CH_3$ | $CH_3$ | F | H | 83:17 |
| 8 | 4-$CH_3$ | $CH_3$ | $CH_3$ | F | H | 86:14 |
| 9 | H | $CH_3$ | $CH_3$ | F | H | 86:14 |
| 10 | 4-$C_2H_5O$ | $CH_3$ | $CH_3$ | F | H | E |
| 11 | 4-F | $CH_3$ | $CH_3$ | H | H | 80:20 |
| 12 | 4-$CF_3$ | $CH_3$ | $CH_3$ | H | H | E |
| 13 | 4-Cl | $CH_3$ | $CH_3$ | H | H | 9:1 |
| 14 | 4-$CH_3$ | $CH_3$ | $CH_3$ | H | H | 4:1 |
| 15 | 3,5-Cl | $CH_3$ | $CH_3$ | H | H | 2:3 |
| 16 | 2-F | $CH_3$ | $CH_3$ | H | H | 17:3 |
| 17 | 3-F | $CH_3$ | $CH_3$ | H | H | 9:1 |
| 18 | 3,4-$F_2$ | $CH_3$ | $CH_3$ | H | H | 13:7 |
| 19 | 4-F | $CH_2-CH_2$ | | H | H | E |
| 20 | 4-F | $CH_2-CH_2$ | | H | H | Z |
| 21 | H | $CH_3$ | $CH_3$ | F | H | Z |
| 22 | 4-Cl | $CH_2-CH_2$ | | H | H | E |
| 23 | 4-Cl | $CH_2-CH_2$ | | H | H | Z |
| 24 | 4-$CH_3O$ | $CH_3$ | $CH_3$ | F | H | E |
| 25 | 4-Cl | $CH_3$ | $CH_3CH_2$ | H | H | E |
| 26 | 4-Cl | $CH_3$ | $C_2H_5$ | H | H | Z |
| 27 | 4-$CF_3$ | $CH_3$ | $CH_3$ | F | H | E |
| 29 | 4-F | $CH_3$ | $CH_3$ | F | Cl | E |
| 30 | 4-Cl | $CH_3$ | $CH_3$ | F | Cl | E |
| 31 | 4-Cl | $CH_3$ | $CH_3$ | H | Cl | E |
| 32 | 4-F | $CH_3$ | $CH_3$ | H | $CH_3$ | E |

TABLE II

| Compound Number | W | $R^1$ | $R^2$ | Y | Z |
|---|---|---|---|---|---|
| 33 | 4-$C_2H_5O$ | $CH_3$ | $CH_3$ | H | H |
| 34 | 4-Cl | $CH_3$ | $CH_3$ | H | H |
| 35 | 4-F | $CH_3$ | $CH_3$ | H | H |
| 36 | 4-$CH_3$ | $CH_3$ | $CH_3$ | H | H |
| 37 | 4-F | $CH_3$ | $CH_3$ | F | H |
| 38 | 4-$CH_3O$ | $CH_3$ | $CH_3$ | F | H |
| 39 | 4-F | $CH_2-CH_2$ | | H | H |
| 40 | 4-Cl | $CH_2-CH_2$ | | H | H |
| 41 | 4-Cl | $CH_3$ | $CH_3$ | F | H |
| 42 | H | $CH_3$ | $CH_3$ | F | H |
| 43 | 4-$CH_3$ | $CH_3$ | $CH_3$ | F | H |

In the following description the group of formula

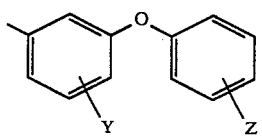

is referred to hereinafter as "R⁴" and the group of formula:

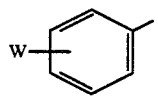

is referred to as "R³".

The compounds of the invention may be prepared by reacting an aldehyde of formula:

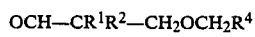

wherein $R^1$, $R^2$ and $R^4$ are as defined hereinabove, with a triphenylphosphonium salt of formula:

$R^3CH_2P(Ph)_3{}^+ \cdot Hal^-$ where $R^3$ is as defined hereinabove and $Hal^-$ represent a halide ion, in the presence of a base e.g. an alkali metal alkoxide, under the conditions of the Wittig reaction. The E and Z isomers may be separated by e.g. chromatographic means.

The invention includes in a further aspect compounds of formula:

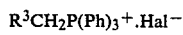

which have not previously been described as useful intermediates in the preparation of the ethers of the invention. They may be prepared by oxidation of novel compounds of formula:

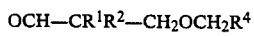

wherein $R^1$, $R^2$ and $R^4$ are as defined hereinabove. A suitable oxidising agent is pyridinium chlorochromate.

In a yet further aspect therefore the invention includes the compounds of formula:

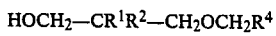

useful as intermediates herein.

These compounds can be prepared by reacting a benzyl halide of formula $R^4$—Q (where Q is halo, preferably chloro or bromo) with a diol of formula:

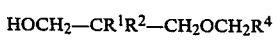

in the presence of a base, e.g. sodium hydride.

The following Scheme illustrates the preparation of E,Z-3,3-dimethyl-1-(4-fluorophenyl)-4-(4-fluoro-3-phenoxybenzyloxy)but-1-ene.

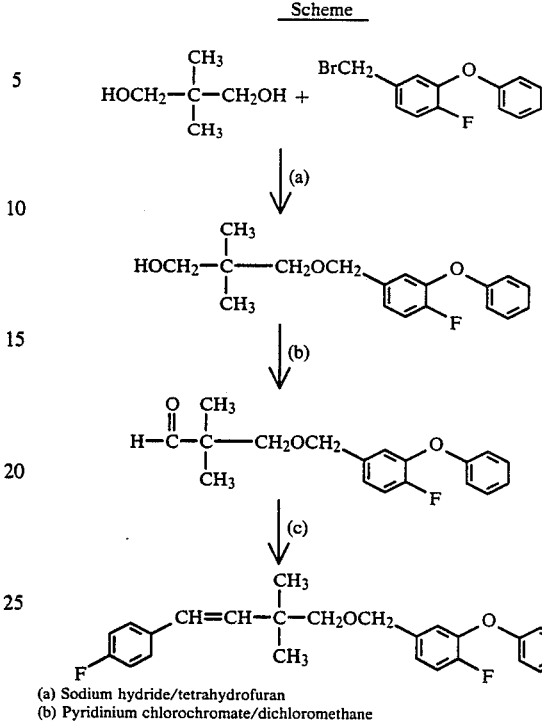

(a) Sodium hydride/tetrahydrofuran
(b) Pyridinium chlorochromate/dichloromethane
(c) 4-fluorophenyltriphenylphosphonium bromide/potassium t-butoxide/diethyl ether The compound of formula I wherein X and $X^1$ each represent hydrogen may be obtained by reduction of the corresponding compounds of formula I wherein X and $X^1$ represent a second bond between the adjacent carbon atoms, by for example, hydrogenation over a metal catalyst such as palladium supported on charcoal.

Further details of the processes for preparing the compounds of the invention may be ascertained from the specific Examples hereinafter.

The compounds of formula I may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence at the locus of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following.
(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-biollethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;
(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphosmethyl, fenitrothion or diazinon;
(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;
(d) Benzoyl ureas such as triflumuron, chlorofluazuron;
(e) Organic tin compounds such as cyhexatin, fenbutatin oxide, azocyclotin;
(f) Macrolides such as avermectins or milbemyins, for example such as abamectin, avermectin, and milbemycin;
(g) Hormones such as juvenile hormone, juvabione, or ecdysones;
(h) Pheromones;
(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentazine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:

*Myzus persicae* (aphids)
*Aphis fabae* (aphids)
*Megoura viceae* (aphids)
*Aedes aegypti* (mosquitoes)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
*Tetranychus cinnabarinus* (carmine spider mite)
*Tetranychus urticae* (red spider mites)
*Aonidiella* spp. (scale insects)
*Trialeuroides* spp. (white flies)
*Blattella germanica* (cockroaches)
*Spodoptera littoralis* (cotton leaf worm)
*Heliothis virescens* (tobacco budworms)
*Chortiocetes terminifera* (locusts)
*Diabrotica* spp. (rootworms)
*Agrotis* spp. (cutworms)
Chilo partellus (maize stem borers)
Nilaparvata lugens (plant hoppers)

The compounds of formula I and compositions comprising them have shown themselves to be particularly useful in controlling pests of maize and rice such as Chilo (stem borers) as well as lepidopteran pests of cotton, for example Spodoptera spp. and Heliothis spp.

Although all of the invention compounds of formula I show insecticidal properties in the tests described hereinafter in the Examples they are not all equally effective at the particular rates tested to all of the test species.

Some of the compounds are particularly useful for the control of insect pests of rice because they show high levels of activity against rice pests such as Chilo sp. and Nilaparvata sp. at rates which are not toxic to fish, thus enabling their use in paddy rice where fish are cultivated in the paddy.

The various aspects of the invention are illustrated in the following Examples.

EXAMPLE 1

This Example illustrates the preparation of 1,1-di(hydroxymethyl)cyclopropane.

A solution of diethyl-1,1-cyclopropane-dicarboxylate (10 g) in tetrahydrofuran (25 cm$^3$) was added dropwise to a stirred suspension of lithium aluminium hydride (2.15 g) in tetrahydrofuran (75 cm$^3$) whilst the reaction temperature was maintained below 20° C. When the addition was complete the mixture was allowed to warm to the ambient temperature (ca. 25° C.), and allowed to stir for a further 2 hours. A saturated solution of sodium potassium tartrate was then added carefully to the reaction mixture, which was then allowed to stand for 18 hours. The mixture was extracted into ethylacetate several times and the combined extracts dried over anhydrous magnesium sulphate. Removal of the solvent by evaporation gave 1,1-di(hydroxymethyl)cyclopropane (3 g).

$^1$H nmr (CDCl$_3$) ppm: 0.5 (s,4H); 2.7 (broad s,2H); and 3.6 (s,4H).

Infra red (liquid film): 3400 and 1020 cm$^{-1}$.

EXAMPLE 2

This Example illustrates the preparation of 1-hydroxymethyl-1-(3-phenoxybenzyloxymethyl)cyclopropane.

A solution of 1,1-dihydroxymethylcyclopropane (3 g) in tetrahydrofuran (20 cm$^3$) was added dropwise to a suspension of sodium hydride (0.35 g) in tetrahydrofuran (30 cm$^3$). After effervescence has ceased, tetrabutylammonium iodide (1g) was added to the grey suspension followed by a solution of 3-phenoxybenzyl bromide (3.88 g) in tetrahydrofuran (15 cm$^3$) at the ambient temperature and the mixture stirred for a further 2 hours. The mixture was poured into water and extracted with ethylacetate. The extracts were combined, dried over magnesium sulphate and concentrated by evaporation of the solvent, and the residual oil purified by column chromatography using a silica gel column eluting first with dichloromethane, followed then by ethylacetate, to give 1-hydroxymethyl-1-(3-phenoxybenzyloxymethyl)cyclopropan-1-ol (1.7 g).

$^1$H nmr (CDCL$_3$) ppm: 0.5 (s,4H); 2.45 (broad s,1H); 3.4 (s,2H); 3.5 (s,2H): 4.5 (s,2H); and 6.9–7.5 (m,9H).

Infra red (liquid film): 3450, 1575, 1475, 1245 and 680 cm $^{-1}$ (major peaks only).

EXAMPLE 3

This Example illustrates the preparation of 2,2-dimethyl-3-(3-phenoxybenzyloxy)propan-1-ol.

A solution of 2,2-dimethylpropan-1,3-diol (15.6 g) in tetrahydrofuran (100 cm$^3$) was added in small aliquots to a stirred suspension of sodium hydride (1.8 g) in tetrahydrofuran (100 cm$^3$) with cooling. After effervescence had ceased, tetra-n-butylammonium iodide (5 g) was added to the resultant grey suspension followed by addition of solution of 3-phenoxybenzyl bromide (19.7 g) in dry tetrahydrofuran (100 cm$^3$) at the ambient temperature (ca. 25° C.), and the mixture stirred for a further 2 hours. The mixture was poured into water and extracted with ethyl acetate. The extracts were combined, dried over anyhydrous magnesium sulphate and concentrated by evaporation of the solvent. The residual oil was identified as a mixture of 2,2-dimethyl-3-(3-phenoxybenzyloxy)propan-1-ol and 2,2-dimethylpropan-1,3-diol by nmr and infra red spectroscopic examination. $^1$H nmr (CDCl$_3$) ppm: 0.9 (s,6H); 2.4 (broad s,1H); 3.3 (s,2H); 3.5 (broad d,1H); 4.5 (s,2H); and 6.8–7.5 (m,9H).

Infra red (liquid film): 3340, 1585, 1490 and 1255 cm$^{-1}$.

EXAMPLE 4

This Example illustrates the preparation of 2-ethyl-2-methyl-3-(3-phenoxybenzyloxy)propan-1-ol.

2-Ethyl-2-methylpropan-1,3-diol (9.44 g) was reacted according to the procedure laid out in Example 2 to give the crude product as an impure oil. Distillation through a kugelrohr apparatus give two fractions. The first being 44% by gas chromatography the desired compound whilst the second fraction (B. pt. 200° C./0.03 mmHg) was the desired 2-ethyl-2-methyl-3-(3-phenoxybenzyloxy)propan-1-ol (3.6 g).

$^1$H nmr (CDCl$_3$) ppm: 0.8 (m,6H); 1.4 (m,2H); 2.5 (broad s,1H); 3.4 (s,2H); 3.5 (broad s,2H); 4.5 (s,2H); and 6.9-7.5 (m,9H).

Infra red (liquid film): 3450, 1590, 1490, 1260, 1220, and 695 cm$^{-1}$ (major peaks only).

EXAMPLE 5

This Example illustrates the preparation of 2,2-dimethyl-3-(4-fluoro-3-phenoxybenzyloxy)propan-1-ol.

A solution of 2,2-dimethylpropan-1,3-diol (5.2 g) in tetrahydrofuran (35 cm$^3$) was added in a small aliquots to a stirred suspension of sodium hydride (0.6 g) in tetrahydrofuran (35 cm$^3$) with cooling. After effervescence had ceased tetrabutylammonium iodide (1.7 g) was added to the resultant grey suspension followed by addition of a solution of 4-fluoro-3-phenoxybenzyl bromide (7.1 g) in dry tetrahydrofuran (30 cm$^3$) at the ambient temperature (ca. 25° C.), and the mixture stirred for a further 2 hours. The mixture was poured into water and extracted with ethyl acetate. The extracts were combined, dried over anhydrous magnesium sulphate and concentrated by evaporation of the solvent and the residual oil identified as a mixture of 2,2-dimethyl-3-(4-fluoro-3-phenoxybenzyloxy)propan-1-ol and some unreacted 2,2-dimethylpropan-1,3-diol by nmr and infra red spectroscopic examination.

$^1$H nmr (CDCl$_3$) ppm: 0.9 (s,6H); 2.2 (broad s,1H); 3.3 (s,2H); 3.5 (s,2H); 4.4 (s,2H); and 6.9-7.4 (m,8H).

Infra red (liquid film): 3400, 1595, 1515, 1280, 1215 cm$^{-1}$ (major peaks only).

EXAMPLE 6

This Example illustrates the preparation of 2,2-dimethyl-3-(3-phenoxybenzyloxy)propan-1-al.

A solution of 2,2-dimethyl-3-(3-phenoxybenzyloxy)-propan-1-ol (15 g) in dry dichloromethane (50 cm$^3$) was added dropwise to a stirred suspension of pyridinium chlorochromate (18.75 g) in dichloromethane (100 cm$^3$) whilst the reaction temperature was maintained within the range 0°-5° C. When the addition was complete, the mixture was allowed to warm to the ambient temperature (ca. 25° C.) over a period of 2 hours. After the reaction mixture had been diluted with diethyl ether, the ethereal layer was decanted and filtered through celite. The solvent was removed by evaporation and the residual oil purified by column chromatography using a silica gel column and eluting with dichloromethane as eluent, to yield 2,2-dimethyl-3-(3-phenoxybenzyloxy)-propane-1-al (7.2 g) as an orange oil.

1H nmr (CDCl$_3$) ppm: 1.1 (s,6H); 3.45 (s,2H); 4.5 (s,2H); 6.8-7.4 (m,9H); and 9.55 (s,1H).

Infra red (liquid film): 1735, 1590, 1490, 1445, 1250, 1215, 1100 and 690 cm$^{-1}$.

EXAMPLE 7

This Example illustrates the preparation of 2-ethyl-2-methyl-3-(3-phenoxybenzyloxy)propan-1-al.

2-Ethyl-2-methyl-3-(3-phenoxybenzyloxy)propan-1-ol (3.6 g) was reacted according to the procedure in Example 6. The crude product was distilled through a kugelrohr apparatus to give 2-ethyl-2-methyl-3-(3-phenoxybenzyloxy)-propan-1-al (2.35 g) (Bpt 170° C./0.07 mm Hg).

$^1$H nmr (CDCl$_3$) ppm: 0.8 (t,3H); 1.05 (s,3H); 1.55 (m,2H); 3.4 (d,1H); 3.5 (d,1H); 4.45 (s,2H); 6.9-7.4 (m,9H); and 9.5 (s,1H).

Infra red (liquid film): 1730, 1590, 1490, 1260, 1220, and 695 cm$^{-1}$.

EXAMPLE 8

This Example illustrates the preparation of 1-formyl-1-(3-phenoxybenzyloxymethyl)cyclopropane.

A solution of dry dimethyl sulphoxide (0.87 g) in dichloromethane (12 cm$^3$) was added dropwise to a stirred solution of oxalyl chloride (0.75 g) in dichloromethane (12 cm$^3$) maintained at −70° C. After a period of five minutes had elapsed, a solution of 2-cyclopropyl-3-(3-phenoxybenzyloxy)propane-1-ol (1.45 g) in dichloromethane (6 cm$^3$) was added dropwise, followed by triethylamine (2.3 g) five minutes later. When the addition was complete the mixture was allowed to warm to the ambient temperature over a period of 2 hours. The reaction mixture was poured into water, and extracted with diethyl ether. The extracts were combined, dried over anhydrous magnesium sulphate and concentrated by evaporation of the solvent. The residual oil (1.5 g) was purified by column chromatography using a silica gel column and eluting with dichloromethane to yield 1-formyl-1-(3-phenoxybenzyloxymethyl)cyclopropane (1 g).

$^1$H nmr (CDCl$_3$) ppm: 1.2 (m,4H); 3.7 (s,2H); 4.5 (s,2H); 6.9-7.4 (m,9H); and 9.0 (s,1H).

Infra red (liquid film): 1715, 1590, 1490, 1260, 1220, and 1100 cm$^{-1}$.

EXAMPLE 9

This Example illustrates the preparation of 2,2-dimethyl-3-(4-fluoro-3-phenoxybenzyloxy)propan-1-al.

A solution of 2,2-dimethyl-3-(4-fluoro-3-phenoxybenzyloxy)propan-1-ol (5.0 g) in dichloromethane (30 cm$^3$) was added dropwise to a stirred suspension of pyridinium chlorochromate (6.77 g) in dichloromethane (20 cm$^3$) whilst the reaction temperature was maintained within the range 0°-5° C. When the addition was complete the mixture was allowed to warm to the ambient temperature over a period of 2 hours. The solvent was removed and the residual oil (3.0 g) purified by column chromatography using a silica gel column and eluting with a 10:1 (by volume) mixture mixture of petroleum ether (boiling range 40°-60°) and diethyl ether to yield 2,2-dimethyl-3-(4-fluoro-3-phenoxybenzyloxy)propan-1-al (1.5 g) as a yellow oil.

$^1$H nmr (CDCl$_3$) ppm: 1.1 (s,6H); 3.5 (s,2H); 4.5 (s,2H);

7.0-7.5 (m,8H); 9.6 (s,1H). Infra red (liquid film): 1735, 1590, 1510, 1490, 1280, 1210 cm$^{-1}$ (major peaks only).

EXAMPLE 10

This Example illustrates the preparation of 3,3-dimethyl-4-(4-fluoro-3-phenoxybenzyloxy)but-1-ene.

Methyltriphenylphosphonium bromide (3 g) was added in portions to a stirred suspension of potassium t-butoxide (0.92 g) in dry diethyl ether (25 cm$^3$), and the resultant mixture stirred for 30 minutes after which a solution of 2,2-dimethyl-3-(4-fluoro-3-phenoxybenzyloxy)propan-1-al (2.5 g) in diethyl ether (25 cm$^3$) was added to the mixture.

An exotherm was noted, and after 10 minutes the mixture was poured into water, and extracted with ethylacetate, the extracts combined, washed with water and dried over anhydrous magnesium sulphate, and concentrated by evaporation of the solvent to yield a yellow oil. This was flash chromatographed on a silica gel column with dichloromethane as eluent to yield 2,2-dimethyl-1-(4-fluoro-3-phenoxybenzyloxy)but-3-ene (1.6 g) as a pale yellow liquid.

$^1$H nmr (CDCl$_3$) ppm: 1.0 (s,6H); 3.2 (s,2H); 4.4 (s,2H); 4.95 (m,2H); 5.8 (dd,1H); and 7.0–7.4 (m,8H).

Infra red (liquid film): 2980, 1590, 1515, 1490, 1285, 1215, and 690 cm$^{-1}$.

EXAMPLE 11

This Example illustrates the preparation of 4-fluorobenzyltriphenylphosphonium bromide.

A solution of 3-fluorobenzyl bromide (4.73 g) in dry toluene (5.0 cm$^3$) was added to a stirred suspension of triphenylphosphine (4.87 g) in dry toluene (5.0 cm$^3$) and after 30 minutes the resultant precipitate was collected by filtration and washed with toluene to yield 4-fluorobenzyltriphenylphosphonium bromide (7.1 g) as a white solid.

$^1$H nmr (CDCl$_3$) ppm: 5.15 (d,2H); 6.8–7.2 (m,4H); 7.5–7.9 (m,15H).

EXAMPLE 12

The following compounds were prepared in an analogous manner to that described in Example 11 from the appropriate benzyl halide and triphenylphosphine.

4-Chlorobenzyltriphenylphosphonium bromide from 4-chlorobenzylbromide.

$^1$H nmr (CDCl$_3$) ppm: 5.50 (d,2H); 7.1 (s,4H); and 7.5–8.0 (m,15H). 4-Methylbenzyltriphenylphosphonium bromide from 4-methylbenzylbromide.

$^1$H nmr (CDCl$_3$) ppm: 2.2 (d,3H); 5.3 (d,2H); and 7.0–8.0 (m,19H). 4-Trifluoromethylbenzyltriphenylphosphonium bromide from 4-trifluoromethylbenzylbromide.

$^1$H nmr (CDCl$_3$) ppm: 5.85 (d,2H) and 7.0–8.0 (m,19H).

3,5-Dichlorobenzyltriphenylphosphonium bromide from 3,5-dichlorobenzylbromide.

-$^1$H nmr (CDCl$_3$) ppm: 5.5 (d,2H); and 7.05–7.8 (m,18H).

2-Fluorobenzyltriphenylphosphonium bromide from 2fluorobenzyl bromide.

$^1$H nmr (CDCl$_3$) ppm: 5.5 (d,2H); 6.7–7.3 (m,3H); and 7.4–8.0 (m,16H).

3-Fluorobenzyltriphenylphosphonium bromide from 3-fluorobenzyl bromide.

$^1$H nmr (CDCl$_3$) ppm: 5.35 (d,2H); 6.7–7.3 (m,3H); and 7.5–8.0 (m,16H).

3,4-Difluorobenzyltriphenylphosphonium bromide from 3,4-difluorobenzylbromide.

$^1$H nmr (CDCl$_3$) ppm: 5.7 (d,2H), 6.7–7.2 (m,2H); and 7.5–8.0 (m,16H).

4-Ethoxybenzyltriphenylphosphonium chloride from 4-ethoxybenzylchloride.

$^1$H nmr (CDCl$_3$) ppm: 1.35 (t,3H); 3.9 (q,2H); 5.3 (d,2H); 6.5 (d,2H); 6.9 (dd,2H); and 7.5 (m,15H).

EXAMPLE 13

This Example illustrates the preparation of 4-ethoxybenzyl chloride.

4-Ethoxybenzyl alcohol (5 g) and concentrated hydrochloric acid (8.5 cm$^3$) were vigorously stirred together for 30 minutes. The 2 phases were then allowed to separate, and the lower layer separated off, and diluted with chloroform. The organic solution was dried over anhydrous magnesium sulphate, and removal of the solvent by evaporation gave 4-ethoxybenzyl chloride (5.6 g). (This product is not stable on keeping, so was converted immediately to the phosphonium salt—see Example 12).

$^1$H nmr (CDCl$_3$) ppm: 1.3 (t,3H); 4.0 (q,2H); 4.6 (s,2H); 6.9 (d,2H); and 7.3 (d,2H).

EXAMPLE 14

This Example illustrates the preparation of 3,5-dichlorobenzyl bromide.

A solution of triphenylphosphine (8.1 g) in diethyl ether (100 cm$^3$) was added to a stirred solution of 3,5-dichlorobenzyl alcohol (5 g) and 1,2-dibromotetrachloroethane (9.9 g) in diethyl ether whilst maintaining the reaction temperature below 5° C. When the addition was complete the reaction mixture was allowed to warm to the ambient temperature (ca. 25° C.), and the mixture stirred for a further 2 hours. The precipitated solid was removed by filtration, and the filtrate concentrated by evaporation of the solvent to give 3,5-dichlorobenzyl bromide (6.8 g).

$^1$H nmr (CDCl$_3$): 4.4 (s,2H); 7.3 (s,3H).

EXAMPLE 15

This Example illustrates the preparation of 3,3-dimethyl-1-(4-fluorophenyl)-4-(4-fluoro-3-phenoxybenzyloxy)but-1-ene.

4-Fluorobenzyltriphenylphosphonium bromide (0.79 g) was added in small portions to a stirred suspension of potassium t-butoxide (0.2 g) in dry diethylether (4.0 cm$^3$) and the resultant mixture stirred for 30 minutes after which a solution of 2,2-dimethyl-3-(4-fluoro-3-phenoxybenzyloxy)propan-1-al (0.5 g) in diethyl ether (4.0 cm$^3$) was added to the mixture. After a further one hour the mixture was poured into water and extracted with ethyl acetate, the extracts combined, washed with water and dried over anhydrous magnesium sulphate, and concentrated by evaporation of the solvent to yield a white solid (1.0 g). This was flash chromatographed on a silica gel column with dichloromethane to yield 3,3-dimethyl-1-(4-fluoro-3-phenoxybenzyloxy)but-1-ene (0.45 g) as a colourless oil, identified by nmr spectroscopy as a mixture of the Z and E isomers (ratio 3:1).

$^1$H nmr (CDCl$_3$) ppm: 0.9, 1.1 (2s,6H); 3.05, 3.2 (2s,2H); 4.3, 4.45 (2s,2H); 5.6 and 6.4, and 6.15 and 6.3, (2×ABq, 2H); 6.8–7.4 (m,12H).

Infra red (liquid film): 1590, 1510, 1490, 1215 cm$^{-1}$ (major peaks only).

The Z and E isomers were separated by hplc using a automated Gilson apparatus fitted with a silica gel column of dimensions 2.5×42 cm, using petroleum ether (boiling range 40°–60°) containing 1% (by volume) diethyl ether as eluent, and a flow rate of 30 cm$^3$/minute. Both were obtained as clear oils.

Isomer A (identified as 100% Z isomer)

$^1$H nmr (CDCl$_3$) ppm: 0.9 (s,6H); 3.1 (s,2H); 4.3 (s,2H); 5.6, 6.4 (d,2H, J=12.5 Hz); 6.9–7.4 (m,12H).

Isomer B (identified as mixture of 87% E-isomer and 13% Z-isomer)

$^1$H nmr (CDCl$_3$) ppm: 1.1 (s,6H); 3.25 (s,2H); 4.45 (s,2H);

6.1, 6.3 (d,2H, J=16.2 Hz); 6.9–7.4 (m,12H).

EXAMPLE 16

The following compounds were prepared in an analogous manner to that described in Example 15 from the appropriate benzyltriphenylphosphonium salts and the appropriate aldehyde.

(i) 3,3-Dimethyl-1-(4-chlorophenyl)-4-(3-phenoxybenzyloxy)but-1-ene from 4-chlorophenyl-triphenylphosphonium bromide and 2,2-dimethyl-3-(3-phenoxybenzyloxy)-propan-1al. The product was identified by nmr spectroscopy as a mixture of the Z and E isomers (ratio 2:1), which were separated as before using hexane containing 1.5% (by volume) diethyl ether as eluent.

Isomer A (identified as 86% Z isomer)
$^1$H nmr (CDCl$_3$) ppm: 0.9 (s,6H); 3.1 (s,2H); 4.4 (s,2H); 5.6 (d,1H); 6.4 (d,1H); and 6.9–7.4 (m,13H).

Isomer B (identified as 90% E isomer)
$^1$H nmr (CDCl$_3$) ppm: 1.1 (s,6H); 3.25 (s,2H); 4.5 (s,2H); 6.2 (d,1H); 6.3 (d,1H); and 6.9–7.4 (m,13H).

(ii) 3,3-Dimethyl-1-(4-chlorophenyl)-4-(4-fluoro-3-phenoxybenzyloxy)but-1-ene from 4-chlorobenzyltriphenyl-phosphonium bromide and 2,2-dimethyl-3-(4-fluoro-3-phenoxybenzyloxy)propan-1-al. The product isomers were separated as before using hexane containing 1.5% diethyl ether (by volume) as eluent.

Isomer A (identified as 90% Z isomer)
$^1$H nmr (CDCl$_3$) ppm: 0.9 (s,6H); 3.1 (s,2H); 4.35 (s,2H); 5.6 (d,1H); 6.4 (d,1H); and 7.0—7.4 (m,12H).

Isomer B (identified as 85% E isomer)
$^1$H nmr (CDCl$_3$) ppm: 1.1 (s,6H); 3.2 (s,2H); 4.45 (s,2H); 6.2 (d,1H); 6.3 (d,1H); and 7.0–7.4 m,12H).

(iii) 3,3-Dimethyl-1-[4-methylphenyl]-4-(4-fluoro-3-phenoxybenzyloxy)but-1-ene from 4-methylbenzyltriphenylphosphonium bromide and 2,2-dimethyl-3-(4-fluoro-3-phenoxybenzyloxy)propan-1-al. The product was identified as a mixture of Z and E isomers (ratio 1:1) by gas chromatography, which were separated as before using hexane containing 1.5% diethyl ether (by volume) as eluent.

Isomer A (identified as 95% Z isomer)
$^1$H nmr (CDCl$_3$) ppm: 0.95 (s,6H); 2.3 (s,3H); 3.1 (s,2H); 4.3 (s,2H); 5.55 (d,1H); 6.45 (d,1H); and 6.95–7.4 (m,12H).

Isomer B (identified as 86% E isomer)
$^1$H nmr (CDCl$_3$) ppm: 1.1 (s,6H); 2.3 (s,3H); 3.25 (s,2H); 4.45 (s,2H); 6.15 (d,1H); 6.30 (d,1H); and 6.9–7.3 (m,12H).

(iv) 3,3-Dimethyl-1-phenyl-4-(4-fluoro-3-phenoxybenzyloxy)but-1-ene from benzyltriphenylphosphonium bromide and 2,2-dimethyl-3-(4-fluoro-3-phenoxybenzyloxy)propan-1-al. The product was identified as a mixture of the Z and E isomers (ratio 1:1) by gas chromatography which were separated as before using hexane containing 1.5% diethyl ether (by volume) as eluent.

Isomer A (identified as 95% Z isomer)
$^1$H nmr (CDCl$_3$) ppm: 0.95 (s,6H); 3.1 (s,2H); 4.3 (s,2H); 5.55 (d,1H); 6.5 (d,1H) and 6.95–7.4 (m,13H).

Isomer B (identified as 86% E isomer) p $^1$H nmr (CDCl$_3$) ppm: 1.1 (s,6H); 3.25 (s,2H); 4.45 (s,2H); 6.2 (d,1H); 6.3 (d,1H); and 6.9–7.4 (m,13H).

(v) 3,3-Dimethyl-1-(4-ethoxy-phenyl)-4-(4-fluoro-3-phenoxybenzyloxy)but-1-ene from 4-ethoxyphenyltriphenyl-phosphonium chloride and 2,2-dimethyl-3-[4-fluoro-3-phenoxybenzyloxy)prop-1-al. The product was identified as a mixture of the Z and E isomers (ratio 1:1) by gas chromatography, which were separated as before using hexane containing 1.5% diethyl ether (by volume) as eluent.

Isomer A (identified as 90% Z isomer)
$^1$H nmr (CDCl$_3$) ppm: 0.95 (s,6H); 1.4 (t,3H); 3.1 (s,2H); 4.0 (q,2H); 4.3 (s,2H); 5.5 (d,1H); 6.4 (d,1H); and 6.7–7.4 (m,12H).

Isomer B (identified as 90% E isomer)
$^1$H nmr (CDCl$_3$) ppm: 1.1 (s,6H); 1.3 (t,3H); 3.25 (s,2H); 4.00 (q,2H); 4.4 (s,2H); 6.1 (d,1H); 6.25 (d,1H); and 6.7–7.4 (m,12H).

(vi) 3,3-Dimethyl-1-(4-ethoxyphenyl)-4-(3-phenoxybenzyloxy)but-1-ene from 4-ethoxyphenyltriphenylphosphonium chloride and 2,2-dimethyl-3-(3-phenoxybenzyloxy)propan-1al. The product was identified as a mixture of the Z and E isomers (ratio 1:1) by gas chromatography, which were separated as before using hexane containing 1.5% diethyl ether (by volume) as eluent.

Isomer A (identified as 100% Z isomer)
$^1$H nmr (CDCl$_3$) ppm: 0.95 (s,6H); 1.4 (t,3H); 3.15 (s,2H); 4.0 (q,2H); 4.4 (s,2H); 5.55 (d,1H); 6.45 (d,1H); and 6.7–7.4 (m,13H).

Isomer B (identified as 88% E isomer)
$^1$H nmr (CDCl$_3$) ppm: 1.1 (s,6H); 1.4 (t,3H); 3.25 (s,2H); 4.0 (q,2H); 4.5 (d,2H); 6.1 (d,1H); 6.3 (d,1H); and 6.7–7.4 (m,13H).

(vii) 3,3-Dimethyl-1-(4-fluorophenyl)-4-(3-phenoxybenzyloxy)but-1-ene from 4-fluorophenyltriphenylphosphonium bromide and 2,2-dimethyl-3-(3-phenoxybenzyloxy)propan-1-al. The product was identified as a mixture of the Z and E isomers (ratio 2:1) by gas chromatography, which wer separated as before using hexane containing 1.5% diethyl ether (by volume) as eluent.

Isomer A (identified as 90% Z isomer)
$^1$H nmr (CDCl$_3$) ppm: 0.9 (s,6H); 3.1 (s,2H); 4.4 (s,2H); 5.6 (d,1H); 6.45 (d,1H); and 6.9–7.4 (m,13H).

Isomer B (identified as 80% E isomer)
$^1$H nmr (CDCl$_3$) ppm: 1.1 (s,6H); 3.25 (s,2H); 4.5 (s,2H); 6.15 (d,1H); 6.30 (d,1H); and 6.9–7.4 (m,13H).

(viii) 3,3-Dimethyl-1-(4-methylphenyl)-4-(3-phenoxybenzyloxy)but-1-ene from 4-methylphenyltriphenylphosphonium bromide and 2,2-dimethyl-3-(3-phenoxybenzyloxy)propan-1-al. The product was identified as a mixture of Z and E isomers (ratio 1:1) by gas chromatography, which were separated as before using hexane containing 1.5% diethyl ether (by volume) as eluent.

Isomer A (identified as 80% Z isomer)
$^1$H nmr (CDCl$_3$) ppm: 0.9 (s,6H); 2.3 (s,3H); 3.15 (s,2H); 4.4 (s,2H); 5.55 (d,1H); 6.45 (d,1H); and 6.9–7.4 (m,13H).

Isomer B (identified as 80% E isomer)
$^1$H nmr (CDCl$_3$) ppm: 1.1 (s,6H); 2.3 (s,3H); 3.2 (s,2H); 4.5 (s,2H); 6.2 (d,1H); 6.3 (d,1H); and 6.9–7.4 (m,13H).

(ix) 3,3-Dimethyl-1-(3,5-dichlorophenyl)-4-(3-phenoxybenzyloxy)but-1-ene from 3,5-dichlorophenyltriphenylphosphonium bromide and 2,2-dimethyl-3-(3-phenoxybenzyloxy)propan-1-al. The product was identified as a mixture of Z and E isomers (ratio 3:2) by gas chromatography. The isomers could not be separated.
$^1$H nmr (CDCl$_3$) ppm: 0.9, 1.1 (s,6H); 3.1, 3.25 (s,2H); 4.4, 4.5 (s,2H); 5.6, 6.2 (d,1H); 6.25, 6.3 (d,1H); and 6.9–7.4 (m,12H).

(x) 3,3-Dimethyl-1-(2-fluorophenyl)-4-(3-phenoxybenzyloxy)but-1-ene from 2-fluorophenyltriphenylphosohonium bromide and 2,2-dimethyl-3-(3-phenoxyoenzyloxy)propan-1al. The product was identified as a mixture of Z and E isomers (ratio 2:1) by gas chromatography, which were separated as before using hexane containing 1.5% diethyl ether (by volume) as eluent.

Isomer A (identified as 70% Z isomer) 1H nmr (CDCl$_3$) ppm: 0.9 (s,6H); 3.15 (s,2H); 4.4 (s,2H); 5.75 (d,1H); 6.3 (d,1H); and 6.9–7.4 (m,13H).

Isomer B (identified as 85% E isomer) 1H nmr (CDCl₃) ppm: 1.1 (s,6H); 3.3 (s,2H); 4.5 (s,2H); 6.3 (d,1H); 6.5 (d,1H); and 6.9–7.4 (m,13H).

(xi) 3,3-Dimethyl-1-(3-fluorophenyl)-4-(3-phenoxybenzyloxy)but-1-ene from 3-fluorophenyltriphenylphosphonium bromide and 2,2-dimethyl-3-(3-phenoxybenzyloxy)propan-1-al. The product was identified as a mixture of Z and E isomers (ratio 1.4:1) by gas chromatography, which were separated as before using hexane containing 1.5% diethyl ether (by volume) a eluent.

Isomer A (identified as 95% Z isomer)
$^1$H nmr (CDCl₃) ppm: 0.95 (s,6H); 3.15 (s, H); 4.4 (s,2H); 5.6 (d,1H); 6.45 (d,1H); and 6.8–7.4 (m,13H).

Isomer B (identified as 90% E isomer)
1H nmr (CDCl₃) ppm: 1.1 (s,6H); 3.3 (s,2H); 4.5 (s,2H); 6.25 (d,1H); 6.3 (d,1H); and 6.9–7.4 (m,13H).

(xii) 3,3-Dimethyl-1-(3,4-difluorophenyl)-4-(3-phenoxybenzyloxy)but-1-ene from 3,4-difluorophenyltriphenylphosphonium bromide and 2,2-dimethyl-3-(3-phenoxybenzyloxy)propan-1-al. The product was identified as a mixture of Z and E isomers (ratio 2.5:1) by gas chromatography, which were separated as before using hexane containing 1.5% diethyl ether (by volume) as eluent.

Isomer A was not isolated
Isomer B (identified as 65% E isomer)
$^1$H nmr (CDCl₃) ppm: 1.1 (s,6H); 3.3 (s,2H); 4.5 (s,2H); 6.2 (d,1H); 6.25 (d,1H); and 6.9–7.4 (12H).

(xiii) 1-[2-(4-fluorophenyl)ethen-1-yl]-1-(3-phenoxybenzyloxymethyl)cyclopropane from 4-fluorophenyltriphenylphosphonium bromide and 1-formyl-1-(3-phenoxybenzyloxymethyl)cyclopropane The product was identified as a mixture of Z and E isomers (ratio 1.5:1) by gas chromatography;, which were separated as before using hexane containing 1.5% diethyl ether (by volume) as eluent.

Isomer A (identified as 100% Z isomer)
$^1$H nmr (CDCl₃) ppm: 0.45 (m,2H); 0.65 (m,2H); 3.45 (s,2H); 4.5 (s,2H); 5.8 (d,1H); 6.4 (d,1H); and 6.9–7.5 (m,13H).

Isomer B (identified as 100% E isomer) 1H nmr (CDCl₃) ppm: 0.8 (s,4H); 3.5 (s,2H); 4.55 (s,2H); 5.9 (d,1H); 6.4 (d,1H); and 6.9–7.4 (m,13H).

(xiv) 1-[2-(4-chlorophenyl)ethen-1-yl]-1-(3-phenoxybenzyloxymethyl)cyclopropane from 4-chlorophenyltriphenylphosphonium bromide and 1-formyl-1-(3-phenoxybenzyloxymethyl)cyclopropane. The product was identified as a mixture of Z and E isomers (ratio 1.3:1) by gas chromatography, which were separated as before using hexane containing 1.5% diethyl ether (by volume) as eluent.

Isomer A (identified as 100% Z isomer)
$^1$H nmr (CDCl₃) ppm: 0.45 (m,2H); 0.65 (m,2H); 3.45 (s,2H); 4.5 (s,2H); 5.85 (d,1H); 6.4 (d,1H); and 6.9–7.5 (m,13H).

Isomer B (identified as 100% E isomer) 1H nmr (CDCl₃) ppm: 0.8 (s,2H); 3.5 (s,2H); 4.55 (s,2H); 6.0 (d,1H); 6.4 (d,1H); and 6.9–7.4 (m,13H).

(xv) 3-Ethyl-3-methyl-1-(4-chlorophenyl)-4-(3-phenoxybenzyloxy)but-1-ene from 4-chlorophenyltriphenyl-phosphonium bromide and 2-ethyl-2-methyl-3-(3-phenoxybenzyloxy)propan-1-al. The product was identified as a mixture of Z and E isomers (ratio 1.35:1) by gas chromatography, which were separated as before using hexane containing 2% diethyl ether (by volume) as eluent.

Isomer A (identified as 90% Z isomer)
$^1$H nmr (CDCl₃) ppm: 0.8 (t,3H); 0.85 (s,3H); 1.4 (m,2H); 3.15 (2x d,2H); 4.4 (s,2H); 5.5 (d,1H); 6.5 (d,1H); and 6.9–7.4 (m,13H).

Isomer B (identified as 95% E isomer)
$^1$H nmr (CDCl₃) ppm: 0.8 (t,3H); 1.1 (s,3H); 1.45 (m,2H); 3.3 (s,2H); 4.5 (s,2H); 6.15 (d,1H); 6.25 (d,1;H); and 6.9–7.4 (m,13H).

EXAMPLE 17

This Example illustrates the preparation of 3,3-dimethyl-1-(4-trifluoromethylphenyl)-4-(3-phenoxybenzyloxy)but-1-ene.

A suspension of sodium hydride (0.1 g) in dry dimethylsulphoxide (15 cm³) was heated to 65° C. for a period of 1½ hours. After cooling to the ambient temperature (ca. 25° C.) 4-trifluoromethylphenyltriphenylphosphonium bromide (1.75 g) was added in portions, and the mixture was stirred for a further hour. A solution of 2,2-dimethyl-3-(3-phenoxybenzyloxy)propan-1-al in dimethylsulphoxide (15 cm³) was then added, and after stirring for 2 hours, the reaction mixture was poured into water and extracted into ethylacetate. The extracts were combined, washed with water and dried over anhydrous magnesium sulphate, and concentrated by evaporation of the solvent to yield an orange oil. This was flash chromatographed on a silica gel column with dichloromethane as eluent to yield 3,3-dimethyl-1-(4-trifluoromethylphenyl)-4-(3-phenoxybenzyloxy)but-1-ene (0.7 g) as a colourless oil, identified by nmr spectroscopy as an impure mixture of the Z and E isomers (ratio 3:1).

The Z and E isomers were separated in an analogous manner to that described in Example 15 using hexane containing diethyl ether (1.5% by volume) as eluent.

Isomer A (identified as 95% Z isomer)
$^1$H nmr (CDCl₃) ppm: 0.9 (s,6H); 3.1 (s,2H); 4.4 (s,2H); 5.7 (d,1H); 6.5 (d,1H); and 6.9–7.6 (m,13H).

Isomer B (identified as 90% E isomer)
$^1$H nmr (CDCl₃) ppm: 1.1 (s,6H); 3.3 (s,2H); 4.5 (s,2H); 6.4 (s,2H); and 6.8–7.6 (m,13H).

EXAMPLE 18

This Example illustrates the preparation of 3,3-dimethyl-1-(4-methoxyphenyl)-4-(4-fluoro-3-phenoxybenzyloxy)but-1-ene.

A stirred mixture of 3,3-dimethyl-4-(4-fluoro-3phenoxybenzyloxy)but-1-ene (0.27 g), p-iodoanisole (0.21 g), palladium (II) diacetate (0.02 g), tri-o-toluylphosphine (0.054 g) and tetramethylethylenediamine (0.1 g) was heated at 160° C. for 24 hours. After cooling, the mixture was poured into dilute aqueous hydrochloric acid, and extracted into ethyl acetate, the extracts combined, washed with water, dried over anhydrous magnesium sulphate, and concentrated by evaporation of the solvent to yield a brown oil. The crude product was distilled through a kugelrohr apparatus to give 3,3-dimethyl-1-(4-methoxyphenyl)-4-(4-fluoro-3-phenoxybenzyloxy)but-1-ene (0.033 g), as an oil, contained by 30% of 3,3-dimethyl-2(4-methoxyphenyl)-4-(4-fluoro-3-phenoxybenzyloxy)but-1ene.

$^1$H nmr (CDCl₃) ppm: 1.1 and 1.12 (s,6H); 3.15 and 3.25 (s,2H); 3.8 (s,2H); 4.4 and 4.45 (s,2H); 4.85 (s,0.3H); 5.15 (s,0.3H); 6.1 (d,0.7H): 6.3 (d,0.7H); and 6.8–7.4 (m,12H).

Infra red (liquid film): 1620, 1600, 1520, 1500, 1290, 1255, and 1220 cm$^{-1}$.

EXAMPLE 19

This Example illustrates the preparation of 3,3-dimethyl-1-(4-chlorophenyl)-4-(3-phenoxybenzyloxy)-butane.

1% (by weight) Palladium on carbon (0.15 g) was added to a solution of 3,3-dimethyl-1-(4-chlorophenyl)-4-(3-phenoxybenzyloxy)but-1-ene (0.3 g) in ethylacetate (15 cm$^3$). The stirred reaction mixture was then kept under an atmosphere of hydrogen until the uptake of gas had ceased. The reaction mixture was then removed from the hydrogenation apparatus, filtered, and the filtrate concentrated by removal of the solvent by evaporation. The crude residual oil was purified by column chromatography using a silica gel column and eluting with hexane containing ethyl acetate (varying from 5% to 10% by volume) to give 3,3-dimethyl-1-(4-chlorophenyl)-4-(3phenoxybenzyloxy)butane (0.16 g) as a colourless oil. 1H nmr (CDCl$_3$) ppm: 0.95 (s,6H); 1.55 (m,2H); 2.5 (m,2H);

3.2 (s,2H); 4.5 (s,2H); and 6.9–7.4 (m,13H).

Infra red (liquid film): 1590, 1490, 1255, 1215 and 1095 cm$^{-1}$.

EXAMPLE 20

The following compound was made in an analogous manner to that described in Example 19. 3,3-Dimethyl-1-(4-ethoxyphenyl)-4-(3-phenoxybenzyloxy)butane from 3,3-dimethyl-1-(4-ethoxyphenyl)-4-(3-phenoxybenzyloxy)but-1-ene.

$^1$H nmr (CDCl$_3$) ppm: 0.9 (s,6H); 1.4 (t,3H); 1.5 (m,2H); 2.5 (m,2H); 3.2 (s,2H); 4.0 (q,2H); 4.5 (s,2H); and 6.8–7.4 (m,13H).

EXAMPLE 21

The activity of the Product was determined using a variety of insect pests. The product was used in the form of liquid preparations containing 500 or 100 parts per million (ppm) by weight of the Product. The preparations were made by dissolving the Product in acetone and diluting the solutions with water containing 0.01% by weight of a wetting agent sold under the trade name "LISSAPOL" NX until the liquid preparations contained the required concentration of the Product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

In the case of the species *Musca domestica* (housefly), additional tests to determine the knockdown effect of the compounds were performed. Details are given in Table III.

The results of the tests are given in Table IV for each of the Products, at the rate in parts per million given in the second column as a grading of mortality designated as A, B or C wherein A indicates 80–100% mortality or knockdown, B indicates 50–79% mortality or knockdown and C indicates less than 50% mortality or knockdown.

In Table IV the pest organism used is designated by a letter code and the pest species, the support medium or food, and the type and duration of test is given in Table III.

TABLE III

| CODE LETTERS (Table IV) | TEST SPECIES | SUPPORT MEDIUM/FOOD | TYPE OF TEST | DURATION (days) |
| --- | --- | --- | --- | --- |
| TU | *Tetranychus urticae* (red spider mites - adult) | French bean leaf | Contact | 3 |
| MP | *Myzus persicae* (aphids) | Leaf | Contact | 2 |
| NL | *Nilaparvata lugens* (green leaf hopper) | Cabbage leaf | Contact | 6 |
| HV | *Heliothis viriscens* (tobacco budworm) | Cotton leaf | Residual | 3 |
| DB | *Diabrotica balteata* (rootworm larvae) | Filter paper/maize seed | Residual | 3 |
| BG | *Blattella germanica* (cockroach nymphs) | Plastic pot | Residual | 3 |
| MD | *Musca domestica* (houseflies - adults) | Cotton wool/sugar | Contact | 1 |
| MD/KD | *Musca domestica* (houseflies - adults) | Cotton/wool sugar | Knockdown | 4 hours |
| CP | *Chilo partellurs* (Stem borers) | Oil seed rape leaf | Residual | 3 |

"Contact" test indicates that both pests and medium were treated and "residual" indicates that the medium was treated before infestation with the pests.

This Example illustrates the insecticidal properties of the Products of this invention.

TABLE IV

| Compound Number | Rate (ppm) | TU | MP | NL | MD KD | MD | BG | HV | CP | DB |
| --- | --- | --- | --- | --- | --- | --- | --- | --- | --- | --- |
| 1 | 500 | B | C | B | A | B | C | A | A | C |
| 2 | 500 | C | C | C | C | C | C | C | B | C |
| 3 | 500 | C | C | C | C | C | C | C | C | C |
| 4 | 500 | C | C | C | C | C | C | C | C | C |
| 5 | 500 | C | C | C | C | C | C | C | C | C |
| 6 | 500 | B | A | A | A | A | A | A | A | A |
| 7 | 500 | C | A | C | A | A | C | A | A | A |
| 8 | 500 | C | A | A | A | A | B | A | A | A |
| 9 | 500 | C | A | A | A | A | C | A | A | A |
| 10 | 500 | C | B | C | B | B | C | A | A | C |
| 11 | 500 | C | C | A | A | B | C | A | A | B |

TABLE IV-continued

| Compound Number | Rate (ppm) | TU | MP | NL | MD | KD | MD | BG | HV | CP | DB |
|---|---|---|---|---|---|---|---|---|---|---|---|
| 12 | 500 | C | B | A | C | C | B | C | A | C | |
| 13 | 500 | B | A | A | A | B | C | A | A | A | |
| 14 | 500 | C | C | B | C | C | C | A | A | B | |
| 15 | 500 | C | C | C | C | C | C | C | A | C | |
| 16 | 500 | C | C | C | C | C | C | C | C | C | |
| 17 | 500 | C | C | C | C | C | C | A | A | C | |
| 18 | 500 | B | C | C | C | C | C | A | A | C | |
| 19 | 100 | C | C | C | C | C | C | A | C | C | |
| 20 | 500 | C | B | C | C | C | C | C | A | C | |
| 21 | 100 | C | C | C | C | C | C | C | A | C | |
| 22 | 500 | C | C | B | C | C | C | C | A | C | |
| 23 | 500 | C | C | A | C | C | C | C | A | C | |
| 24 | 500 | B | B | A | A | A | C | B | A | C | |
| 25 | 500 | C | B | B | C | B | A | A | — | C | |
| 26 | 500 | C | C | C | C | C | C | C | C | C | |
| 33 | 500 | C | C | C | C | C | C | C | A | C | |
| 34 | 500 | B | C | C | C | C | C | A | A | C | |

I claim:

1. A compound for formula:

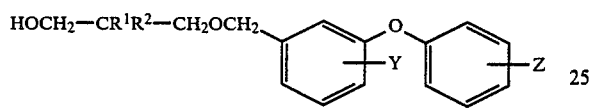

wherein Y represents hydrogen or halogen; Z represents hydrogen, halogen or lower alkyl; and $R^1$ and $R^2$ each represent hydrogen or alkyl of up to four carbon atoms, or $R^1$ and $R^2$ together represent represent an alkylene group of from two to five carbon atoms.

2. A compound of formula:

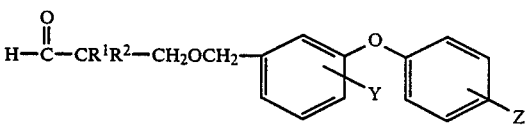

wherein Y represents hydrogen or halogen; Z represents hydrogen, halogen or lower alkyl; and $R^1$ and $R^2$ each represent hydrogen or alkyl of up to four carbon atoms, or $R^1$ and $R^2$ together represent an alkylene group of from two to five carbon atoms.

* * * * *